United States Patent [19]

Beitz et al.

[11] Patent Number: 4,921,710
[45] Date of Patent: May 1, 1990

[54] METHOD OF CONVERTING CHOLESTEROL IN FOOD TO COPROSTANOL

[75] Inventors: Donald C. Beitz; Jerry W. Young; Shangara S. Dehal, all of Ames, Iowa

[73] Assignee: Iowa State University Research Foundation, Inc., Ames, Iowa

[21] Appl. No.: 222,016

[22] Filed: Jul. 21, 1988

[51] Int. Cl.$^5$ .............................................. A23K 1/00
[52] U.S. Cl. ...................................... 426/56; 426/580; 426/641
[58] Field of Search ................ 426/2, 56, 601, 580, 426/641; 514/456; 435/189

[56] References Cited

U.S. PATENT DOCUMENTS

| | | | |
|---|---|---|---|
| Re. 30,910 | 4/1982 | Weigand | 424/238 |
| 2,697,106 | 12/1954 | Shepherd et al. | 260/397.2 |
| 2,813,879 | 11/1957 | Wildi et al. | 260/397.2 |
| 2,838,526 | 6/1956 | Laubach | 260/397.2 |
| 2,840,574 | 6/1958 | Chemerda et al. | 260/397.2 |
| 2,979,440 | 4/1961 | Smythe | 195/64 |
| 3,859,437 | 1/1975 | Weigand | 424/238 |
| 3,959,540 | 5/1976 | Leiberich et al. | 428/35 |
| 4,001,480 | 1/1977 | Shank | 428/411 |
| 4,009,076 | 2/1977 | Green et al. | 195/63 |
| 4,106,991 | 7/1978 | Markussen et al. | 195/63 |
| 4,251,387 | 2/1981 | Lim et al. | 252/316 |
| 4,362,711 | 12/1982 | Cerami | 424/33 |
| 4,482,630 | 11/1984 | Allen et al. | 435/187 |
| 4,492,706 | 1/1985 | Kallai-Sanfacon | 424/270 |
| 4,603,142 | 7/1986 | Burger et al. | 514/456 |
| 4,689,326 | 7/1987 | Hall et al. | 514/217 |

FOREIGN PATENT DOCUMENTS 59-186972  10/1984  Japan ..................................... 309/30

OTHER PUBLICATIONS

Lehninger "Biochemistry" Second Edition Worth Publishers Inc. (1975) p. 685.

*Primary Examiner*—R. B. Penland
*Attorney, Agent, or Firm*—Zarley, McKee, Thomte, Voorhees & Sease

[57] ABSTRACT

Cholesterol reductase was discovered in certain green plant parts. The enzyme is known to be present in several bacteria that commonly inhabit the digestive tract of animals. Eubacteria species A.T.C.C. 21408 is one such cholesterol reductase-containing bacterium. It is concentrated from a homogenate, preferably of leaves of plants or from bacteria or other organisms to provide a cell-free, cholesterol reductase-enriched preparation that can be used to decrease cholesterol content of food substances.

8 Claims, No Drawings

METHOD OF CONVERTING CHOLESTEROL IN FOOD TO COPROSTANOL

BACKGROUND OF THE INVENTION

It is generally recognized that high blood cholesterol concentrations provide a significant risk factor in heart disease. It is also generally recognized that eating foods high in saturated fats, like many red meats may contribute significantly to increased blood cholesterol concentrations in humans. Correspondingly, the increased blood cholesterol concentration in humans seems to have a direct positive correlation with coronary heart disease. Accordingly, there is a continuing and real interest in decreasing the intake of food substances that have high cholesterol content. Thus, there has been in the past years a significant health trend away from red meat, milk products, and eggs.

Accordingly, there is a continuing and real need to develop techniques for decreasing cholesterol concentrations in food substances, and particularly in slaughter animals that are to be used in preparation of table meats and in eggs.

Cholesterol reductase is a known enzyme that catalyzes the chemical reduction of cholesterol to coprostanol. However, heretofore, it has been believed and found that cholesterol reductase is present only in certain bacteria. It has now been discovered that cholesterol reductase is present in certain green plant parts, particularly the leaves of green leafy plants, such as soybeans, corn, and cucumbers. It is believed that the applicants are the first ever to discover and take advantage of the existence of cholesterol reductase in green plant parts.

It is a primary objective of the present invention to provide a method of concentrating cholesterol reductase from green plant parts.

Another primary objective of the present invention is to use cholesterol reductase derived from green plant parts or from bacterial sources such as Eubacteria species A.T.C.C. 21408 to treat food substances that contain cholesterol in order to decrease the concentration of cholesterol therein.

It is a further objective of the present invention to provide a means of decreasing cholesterol concentration in cell membranes of the muscle of meat source animals.

An even further objective of the present invention is to decrease the health risk of people that use red meat and other animal products used as food, such as swine, poultry, fish, eggs, and milk products, by decreasing the cholesterol concentration of the food products.

The method and means of accomplishing each of the above objectives as well as others will become apparent from the detailed description of the invention that follows hereinafter.

SUMMARY OF THE INVENTION

This invention is premised on the discovery that cholesterol reductase can be extracted and concentrated from green plant parts, particularly of cucumbers, soybean, and corn. The process involves homogenizing the green plant parts, separating the fibrous materials from the crude homogenate, and concentrating the homogenate to provide a cell-free, cytosolic, cholesterol reductase-enriched preparation, or ultimately a cholesterol reductase purified to homogeneity. A cholesterol reductase-enriched extract or the purified enzyme may also be prepared from Eubacteria species A.T.C.C. 21408 or other cholesterol reductase-containing bacteria. The enzyme preparation may be used to treat food products to convert cholesterol to coprostanol, thus decreasing the amount of cholesterol in food. In a preferred embodiment of the invention, the enzyme is used to decrease cholesterol concentrations in meat animals, including poultry, by injecting into the animals just before slaughter.

DETAILED DESCRIPTION OF THE INVENTION

In accordance with the process of this invention, cholesterol reductase is extracted from green plant parts by homogenizing the green plant parts in an isotonic aqueous-based buffered salt solution that generally has a pH in the range from about 6.0 to about 7.5.

The discovery of cholesterol reductase as being present in certain green plant parts, particularly the leaves, is believed new. It is believed to be present in all green plant parts, but it is most easily homogenized, separated, and concentrated from the leaves that provide the least cell debris. Particularly preferred plants are members of the grass and legume families. Plants that have been tested successfully from the standpoint of successful isolation of cholesterol reductase are not limited to but do include, cucumbers, soybeans, corn, peas, garden green beans, etc. To date, those that seem to have the greatest concentration and that have been used most successfully, and therefore are preferred include cucumbers, soybeans, and corn.

In the first step of the concentration process of this invention, a homogenate is prepared. The amount of homogenization media is generally from about 2 mL/gr to about 20 mL/gr of green plant part, and generally preferred is from about 5 mL/gr to about 10 mL/gr of leaf parts. Concentration does not, however, appear critical. The homogenization media is an aqueous-based, isotonically buffered salt solution that has a pH from about 6.0 to about 7.5. The preferred pH is from about 6.5 to about 7.0.

Various known isotonic aqueous-based, buffered salt solutions used in plant part homogenization may be successfully employed. For example, the buffered solution may be a phosphate buffer solution or a Tris-buffered solution. Generally speaking, any of those aqueous-based isotonic solutions commercially available that have a buffering capacity within the pH range specified may be employed. However, satisfactory results have been obtained with phosphate buffered solutions, which are therefore preferred.

The usual components in a buffered phosphate solution may also contain compounds known to chelate divalent cations that may have a potential for denaturing the enzyme during purification. It has been found preferable to add a chelating agent for divalent cations to the buffered salt solution. Suitable ones include ethylenediaminetetraacetic acid (EDTA). It is not believed that it is absolutely necessary to have a chelating agent, such as ethylenediaminetetraacetic acid in the homogenization buffered solution, but there may be times when it is useful. Also, reducing agents, such as sodium metabisulfite, ascorbate, and dithiothreitol, are added routinely to the homogenization buffer as insurance against enzyme inactivation during subsequent purification steps. Reducing agents are, however, not essential but only preferred. Generally speaking, where chelating agents for divalent cations such as EDTA are added, the amount present should be a small but effective amount of the buffer solution, generally from 0.05 mM to 0.50 mM, and preferably from 0.05 mM to 0.1 mM. Where reducing agents such as metabisulfite are added, the amount should be from 5 mM to 15 mM.

The plant parts are simply added to the homogenization media described above at the concentrations earlier described, and thereafter homogenized in a conventional homogenizer, for example a top-drive Virtis homogenizer. The homogenization does not appear to be critical time-wise, and satisfactory results can be obtained by using, for example, four bursts of homogenization of approximately 15 seconds each. Thereafter, the homogenate is ready for enzyme purification and concentration.

The homogenate is thereafter filtered, for example, gravity filtered and finally squeezed through a cheesecloth. The residue is then discarded, and the filtrate centrifuged. Centrifuging can be, for example, at 27,000×g for 20 minutes. However, centrifugation is not time-dependent and can generally range from 10 minutes to about 30 minutes. After this centrifuge process, the supernatant of the centrifugation is itself centrifuged, for example at 140,000×g for 1 hour. The resulting supernatant (cytosol) can then be dialyzed against a solution of 5 mM phosphate buffer, at a pH of about 6.5. The buffer may also contain a reducing agent such as 0.5 mM of dithiothreitol and may also contain 10% glycerol for the purpose of stabilization of cholesterol reductase. The dialyzed supernatant contains the concentrated cholesterol reductase-enriched preparation.

Thus, it can be seen that first homogenization occurs, followed by separating of the fibrous materials from the crude homogenate, thereafter concentrating the homogenate to provide a cell-free, cytosolic, cholesterol reductase-enriched preparation.

Cholesterol reductase-containing bacteria can be homogenized by sanification by use of a French press or by mechanical shear. The homogenate can then be treated as described for the plant homogenate to concentrate the cholesterol reductase enzyme.

For commercial production of cholesterol reductase the gene or genes for cholesterol reductase may be transferred into another bacterial species such as *E. coli*. The process would be similar to that now in use for making human insulin, bovine growth hormone, and porcine growth hormone.

It is very conceivable that the concentrate can be further treated to obtain substantially 100% pure cholesterol reductase; however, it has been found that this may not be needed, and that the cell-free, cytosolic, cholesterol reductase-enriched preparation itself may be used for the subsequently described methods of chemically reducing cholesterol to coprostanol.

Coprostanol is normally produced in the intestine of animals. It represents cholesterol that has been hydrogenated. Coprostanol is poorly absorbed by humans, and the reduction of cholesterol to coprostanol is enhanced by the enzymatic activity of cholesterol reductase.

In accordance with the method of decreasing cholesterol concentration in food substances, the method of this invention involves treating the food substance with a green plant derived cell-free, cytosolic, cholesterol reductase enriched preparation or a cholesterol reductase from a bacterial source. This treatment simply enzymatically enhances the chemical reduction of cholesterol to coprostanol. However, because coprostanol is not absorbed, it does not increase the cholesterol concentration in the person consuming the food substance. Thus, the green plant derived cell-free, cytosolic, cholesterol reductase-enriched preparation or the bacterial cholesterol reductase can be successfully used to decrease heart disease risk. It simply involves cellular release of the cholesterol reductase followed by partial purification, and thereafter treating the food substance with the cholesterol reductase-enriched preparation.

In a preferred embodiment of the present invention, it has been discovered that decreasing cholesterol concentration in food animals to be used to provide meat can be effectively accomplished with use of cholesterol reductase. In this operation, the animal is administered intravenously a safe and effective cholesterol reducing amount of the cell-free, cytosolic, cholesterol reductase-enriched preparation. The animal is administered this prior to slaughter, preferably within an hour of slaughter, commonly within 30 minutes of slaughter, and in every instance at least 15 minutes before slaughter. When this is done, the cholesterol reductase significantly decreases the amount of cholesterol present in the cell membranes of the muscle. In most instances, the amount of reduction is at least 50% and in all instances seems to be at least at the 25% level. All meat-producing animals, such as cattle, sheep, swine, and poultry, can be treated by this procedure because they contain cholesterol. It would also be possible to treat fish in a similar manner.

For treatment of milk, the enzyme can be added to homogenized milk. Alternatively, milk may be passed through an enzyme-supporting inert material. For eggs, the enzyme can be injected into the yolk of the whole egg or added to broken egg mixtures of yolk and white. For meats, the enzyme can be added to ground preparations of meats of the several species of animals.

The amount of the cholesterol reductase preparation that may be administered to the animal will vary, depending upon body weight; its effect is, of course, time-dependent between the time of administration and slaughter. However, generally speaking, the amount will be from about 0.01 mg protein/kg of animal body weight to about 2.50 mg protein/kg of animal body weight. Most preferably the amount will be from about 0.05 mg/kg of animal body weight to about 0.5 mg/kg of animal body weight.

The following examples are offered to further illustrate but not limit the process of the present invention.

EXAMPLE 1

Cucumber plants were grown under controlled conditions in a greenhouse. Washed cucumber leaves (3–6 weeks old) were homogenized in sodium/potassium phosphate buffer (100 mM, pH 6.5) containing sucrose (150 mM), sodium metabisulfite (10 mM), ascorbic acid (10 mM), dithiothreitol (5 mM), and ethylenediaminetetraacetic acid (0.1 mM). Polyvinylpolypyrrolidone and XAD-4 were added to the homogenization medium. The crude homogenate was filtered through several layers of cheesecloth, and the filtrate was centrifuged at 27,000×g for 20 min. The resulting supernatant was centrifuged at 140,000×g for 1 h, and the final supernatant was employed as the cholesterol reductase source after dialysis at 4° C. against 10 mM sodium/potassium phosphate buffer (pH 6.5) containing 20 mM 2-[N-morpholino]ethanesulfonic acid, 0.5 mM dithiothreitol, and 10%(v/v) glycerol.

The enzyme solutions were assayed for cholesterol reductase activity by adding radiolabeled cholesterol and a reducing agent (1.0 mM NADH or NADPH). After incubating for 1 h at 37° C., the reaction mixture was cooled to about 4° C. and extracted three times with diethylether. The ether extract, after the addition of unlabelled cholesterol and coprostanol as chromatographic standards, was concentrated under vacuum and chromatographed on a silica gel H thin-layer plate (0.75 mm thickness) in a solvent system of benzene:ethylacetate (5:1). The developed chromatogram was sprayed with a 0.2% ethanolic solution of 2,7-dichlorofluorescein and visualized under ultraviolet light. The appropriate bands were scraped directly into a scintillation vial for determination of radioactivity.

To determine the cellular compartment where cholesterol reductase is located in cucumber leaves, the 27,000×g supernatant, the 27,000×g pellet, the 140,000×g supernatant (cytosol), and the 140,000×g pellet were assayed for activity. The 27,000×g pellet had virtually no activity, whereas the 140,000×g pellet had 10 to 15% as much activity as the 140,000×g supernatant. Reductase activity in the 140,000×g pellet was decreased even further to about 5% when the pellet was suspended in buffer and recentrifuged. Thus, most of the original cholesterol reductase activity was observed in the 140,000×g supernatant. From these observations, it was concluded that the cholesterol reductase activity is located in the cytosol of cucumber leaves.

To obtain preliminary information on the optimal pH of cholesterol reductase, the 140,000×g supernatant was dialyzed and assayed at pH 5.5, 6.0, 6.5, 7.0, and 8.0. The optimal pH was observed to be pH 6.5. In addition, two reducing agents, NADH and NADPH, were assayed for their efficacy in the cholesterol reductase reaction. It was found that NADPH is the preferred reducing agent by a factor of 3 to 4 over NADH at 1.0 mM concentration.

Once preliminary information was determined on the optimal pH and the preferred reducing agent, several different steps for enzyme purification were tested. One method used was ammonium sulfate precipitation because this would not only decrease the volume of homogenate but also would result in some enzyme purification. Saturating the enzyme preparation with up to 100% ammonium sulfate precipitated only 10 to 15% of the original activity. The supernatant, however, contained 150 to 200% of the original activity. This result indicates that cholesterol reductase was not highly hydrophobic and that some inhibiting and/or competing proteins or other factors are removed by ammonium sulfate treatment.

This treatment with polyvinylpolypyrrolidone and XAD-4 resin is preferred to remove phenolic compounds that inhibit several plant enzymes. The two treatment compounds adsorb phenolics and thereby remove them from the test solutions. For further details with regard to techniques that may be employed in purification of plant lipid-metabolizing enzymes, see Loomis et al., "Adsorbent Polystyrene as an Aid in Plant Enzyme Isolation," *Phytochemistry*, Vol. 18, pp. 1049–1054 (1979); Loomis, W. D., "Overcoming Problems of Phenolics and Quinones in the Isolation of Plant Enzymes and Organelles," *Methods of Enzymology*, Vol. 31, pp. 528–545 (1974); and Kohmoto et al., "A Simple Method For Preparing Physiologically Active Mitochondria From Plant Leaves Rich In Oils And Phenolics," *Plant Cell Reports*, 5:54–56 (1986).

EXAMPLE II

Preliminary experiments have used cholesterol oxidase, which is commercially available, as a model enzyme to determine whether cholesterol in milk is accessible to enzymatic attack. Data from these experiments indicate that 80% to 90% of the cholesterol in homogenized, pasteurized, whole milk would be accessible to reduction to coprostanol by cholesterol reductase. Results with raw, whole milk have been more variable but suggest that 60% to 80% of its cholesterol would be accessible to cholesterol reductase.

EXAMPLE III

When beef cattle and other meat-producing animals are treated with the cholesterol reductase concentrate, prepared in the manner of Example I, just prior to slaughter by injection at a level of approximately 0.05 mg/kg of body weight, cholesterol reductase will circulate through the extracellular space of the animal body (minus the digestive system) and interact with extracellular and membranous cholesterol and catalyze its conversion to coprostanol. Because humans absorb coprostanol very poorly, this treatment of meat animals will decrease the concentration of cholesterol in meat and thus result in an effective method for production of low cholesterol meats.

When in Example I, the cucumbers used therein are replaced with corn, peas, soybeans, or other cholesterol-containing reductase plants, similar results are achieved. Likewise in Example III, if the meat source is other than beef such as swine, poultry, or even fish, similar reductions in cholesterol level will be noticed.

It therefore can be seen that the invention accomplishes at least all of its stated objectives.

What is claimed is:

1. A method of decreasing cholesterol concentration in animal origin foods, consisting essentially of: treating cholesterol-containing, animal origin foods
   with a reductase organism
   cell-free, cholesterol reductase-enriched preparation in an amount effective to reduce cholesterol to coprostanol and to substantially lower the cholesterol concentration of the foods.

2. The method of claim 1 wherein said food is a meat.

3. The method of claim 2 wherein a reducing agent is added to said cholesterol reductase-enriched preparation.

4. The method of claim 1 wherein said food is milk.

5. The method of claim 4 wherein a reducing agent is added to said cholesterol reductase-enriched preparation.

6. The method of claim 1 wherein said food is an egg.

7. The method of claim 6 wherein a reducing agent is added to said cholesterol reductase-enriched preparation.

8. The method of claim 1 wherein a reducing agent is added to said cholesterol reductase-enriched preparation.

* * * * *